US008232315B2

(12) United States Patent
Lee et al.

(10) Patent No.: US 8,232,315 B2
(45) Date of Patent: Jul. 31, 2012

(54) METHODS FOR TREATING DRUG ADDICTION AND IMPROVING ADDICTION-RELATED BEHAVIOR

(75) Inventors: Sung James Lee, Montville, NJ (US); Susan Marie Melnick, Parsippany, NJ (US)

(73) Assignee: SK Biopharmaceuticals Co., Ltd., Seoul (KR)

(*) Notice: Subject to any disclaimer, the term of this patent is extended or adjusted under 35 U.S.C. 154(b) by 334 days.

(21) Appl. No.: 12/492,566

(22) Filed: Jun. 26, 2009

(65) Prior Publication Data

US 2010/0331332 A1 Dec. 30, 2010

(51) Int. Cl.
*A01N 47/10* (2006.01)
*A61K 31/27* (2006.01)
*C07C 261/00* (2006.01)
*C07C 269/00* (2006.01)
*C07C 271/00* (2006.01)

(52) U.S. Cl. .................................... 514/478; 560/157
(58) Field of Classification Search .................. 514/478; 560/157
See application file for complete search history.

(56) References Cited

U.S. PATENT DOCUMENTS

| | | | |
|---|---|---|---|
| 5,705,640 | A | 1/1998 | Choi et al. |
| 5,756,817 | A | 5/1998 | Choi et al. |
| 5,955,499 | A | 9/1999 | Choi et al. |
| 6,002,009 | A | 12/1999 | Cereda et al. |
| 6,140,532 | A | 10/2000 | Choi et al. |
| 2010/0093801 | A1 | 4/2010 | Chung et al. |

FOREIGN PATENT DOCUMENTS

| | | |
|---|---|---|
| WO | 99/02494 | 1/1999 |
| WO | 99/55674 | 11/1999 |
| WO | 02/50071 | 6/2002 |
| WO | 02/080928 | 10/2002 |
| WO | 02/100352 | 12/2002 |
| WO | 2004/026868 | 4/2004 |
| WO | 2004/094418 | 11/2004 |
| WO | 2005/021539 | 3/2005 |
| WO | 2005/092882 | 10/2005 |
| WO | 2006/106425 | 10/2006 |

OTHER PUBLICATIONS

Nunes et. al., Journal of the American Medical Association, 2004, American Medical Association, vol. 291, pp. 1887-1896.*
Cami et. al., The New England Journal of Medicine, 2003, Massachusetts Medical Society, vol. 349, pp. 975-986.*
Xu et. al., Bioorganic and Medicinal Chemistry, 2006, Elsevier, vol. 14, pp. 3285-3299.*
Allen, R.P., PhD, et al., "MRI Measurement of Brain Iron in Patients with Restless Legs Syndrome", Neurology, vol. 56, pp. 263-265, Jan. 2001.
Bayard, Max, MD, et al., "Restless Legs Syndrome", American Family Physician, vol. 78, No. 2, pp. 235-240, Jul. 15, 2008.
Ferini-Strambi, Luigi, "Treatment Options for Restless Legs Syndrome", Expert Opin. Pharmacother., vol. 10, No. 4, pp. 545-554, 2009.
Fulda, Stephany, et al., "Dopamine Agonists for the Treatment of Restless Legs Syndrome", Expert Opin. Pharmacother., vol. 6, No. 15, pp. 2655-2666, 2005.
Garcia-Borreguero, Diego, MD, et al., "Circadian Variation in Neuroendocrine Response to L-dopa in Patients with Restless Legs Syndrome", Sleep, vol. 27, No. 4, pp. 669-673, 2004.
Hornyak, Magdolna, "Depressive Disorders in Restless Legs Syndrome", CNS Drugs, vol. 24, No. 2, pp. 89-98, 2010.
Kim, Sung-Wan, MD, et al., "Bupropion May Improve Restless Legs Syndrome", Clin Neuropharmacol, vol. 28, No. 6, pp. 298-301, Nov.-Dec. 2005.
Ondo, William, G., MD, "Restless Legs Syndrome", Neurol Clin, vol. 27, pp. 779-799, 2009.
Stiasny-Kolster, K., et al., "Static Mechanical Hyperalgesia Without Dynamic Tactile Allodynia in Patients with Restless Legs Syndrome", Brain, vol. 127, No. 4, pp. 773-782, 2004.
PCT/KR2009/005863 International Search Report and Written Opinion dated May 28, 2010 (9 pages).
Miklowitz, David, J., et al., "The Psychopathology and Treatment of Bipolar Disorder", Annu. Rev. Clin. Psychol., vol. 2, 2006.
Miller, Christopher, J., et al., "Assessment Tools for Adult Bipolar Disorder", Clin Psychol. (New York), vol. 16, No. 2, pp. 188-201, Jun. 1, 2009.
Minto, Charles, F., et al., "Pharmacokinetics and Pharmacodynamics of Nandrolone Esters in Oil Vehicle: Effects of Ester, Injection Site and Injection Volume", The Journal of Pharmacology and Experimental Therapeutics, vol. 281, No. 1, pp. 93-102, 1997.
Ostro, Marc, J., et al., "Use of Liposomes as Injectable-Drug Delivery Systems", American Journal of Hospital Pharmacy, vol. 46, pp. 1576-1587, Aug. 1989.
Rao, K, "Recent Developments of Collagen-Based Materials for Medical Applications and Drug Delivery Systems", J. Biomater. Sci. Polymer Edn., vol. 7, No. 7, pp. 623-645, 1995.
Rapoport, Stanley, I., et al., "Bipolar Disorder and Mechanisms of Action of Mood Stabilizers", Brain Research Reviews, vol. 61, pp. 185-209, 2009.
Rohatagi, Shashank, PhD, et al., "Pharmacokinetic and Pharmacodynamic Evaluation of Triamcinolone Acetonide After Intravenous, Oral, and Inhaled Administration", J. Clin. Pharmacol., vol. 35, pp. 1187-1193, 1995.
Tjwa, Martin, K. T., MD, "Budesonide Inhaled Via Turbuhaler: A More Effective Treatment for Asthma than Beclomethasone Dipropionate Via Rotahaler", Annals of Allergy, Asthma, & Immunology, vol. 75, pp. 107-111, 1995.
Vieta, Eduard, et al., "Evolving Trends in the Long-Term Treatment of Bipolar Disorder", The World Journal of Biological Psychiatry, vol. 8, No. 1, pp. 4-11, 2007.
Al-Muhammed, J., et al., "In-Vivo Studies on Dexamethasone Sodium Phosphate Liposomes", J. Microencapsulation, vol. 13, No. 3, pp. 293-306, 1996.

(Continued)

*Primary Examiner* — Sreeni Padmanabhan
*Assistant Examiner* — Sarah Pihonak
(74) *Attorney, Agent, or Firm* — Michael Best & Friedrich LLP

(57) ABSTRACT

The invention is directed to a method of treating addiction to drugs of abuse in a subject, comprising administering a therapeutically effective amount of a cabamoyl compound, or pharmaceutically acceptable salt or ester thereof.

10 Claims, 1 Drawing Sheet

OTHER PUBLICATIONS

Azorin, Jean-Michel, et al., "An Update on the Treatment of Bipolar Depression", Expert Opin. Pharmacother., vol. 10, No. 2, pp. 161-172, 2009.

Chengappa, KNR, et al., "Barriers to the Effective Management of Bipolar Disorder: A Survey of Psychiatrists Based in the UK and USA", Bipolar Disorders, vol. 7, suppl.1, pp. 38-42, 2005.

Chonn, Arcadio, et al., "Recent Advances in Liposomal Drug-Delivery Systems", Current Opinion in Biotechnology, vol. 6, pp. 698-708, 1995.

Cousins, David, A., et al., "The Role of Dopamine in Bipolar Disorder", Bipolar Disorders, vol. 11, pp. 787-806, 2009.

Cuellar, Amy, K., et al., "Distinctions Between Bipolar and Unipolar Depression", Clin. Psychol. Rev., vol. 25, No. 3, pp. 307-339, May 2005.

Eyles, J.E., et al., "Oral Delivery and Fate of Poly(lactic acid) Microsphere-encapsulated Interferon in Rats", J. Pharm. Pharmacol, vol. 49, pp. 669-674, 1997.

Frye, Mark, A., et al., "Unmet Needs in Bipolar Depression", Depression and Anxiety, vol. 19, pp. 1999-208, 2004.

Gao, Zhi-Hui, et al., "Controlled Release of a Contraceptive Steroid from Biodegradable and Injectable Gel Formulations: in Vitro Evaluation", Pharmaceutical Research, vol. 12, No. 6, pp. 857-863, 1995.

Harel, Eiran Vadim, MD, et al., "Effectiveness and Safety of Adjunctive Antidepressants in the Treatment of Bipolar Depression: A Review", Isr J Psychiatry Relat Sci, vol. 45, No. 2, pp. 121-128, 2008.

Kessler, Ronald, C., et al., "Lifetime Prevalence and Age-of-Onset Distributions of DSM-IV Disorders in the National Comorbidity Survey Replication", Arch Gen Psychiatry, vol. 62, pp. 593-602 & 768, Jun. 2005.

Kessler, Ronald, C., et al., "Prevalence, Severity and Comorbidity of Twelve-month DSM-IV Disorders in the National Comorbidity Survey Replication (NCS-R)", Arch Gen Psychiatry, vol. 62, No. 6, pp. 617-627, Jun. 2005.

Pharmacology & Toxicology, Nisell et al, Nicotine Dependence, Midbrain Dopamine Systems and Psychiatric Disorders, 1995, pp. 157-162.

Nature, Pontieri et al, Effects of nicotine on the nucleus accumbens and similarity to those of addictive drugs, Jul. 18, 1996, vol. 382, pp. 255-257.

European Journal of Pharmacology, Damsma et al, Lack of tolerance to nicotine-induced dopamine release in the nucleus accumbens, 1989, pp. 363-368.

Proc. Natl. Acad. Sci. USA, Di Chiara et al, Drugs abused by humans preferentially increase synaptic dopamine concentrations in the mesolimbic system of freely moving rats, Jul. 1988, vol. 85, pp. 5274-5278.

European Journal of Pharmacology, Imperato et al, Nicotine preferentially stimulates dopamine release in the limbic system of freely moving rats, 1986, pp. 337-338.

Pharmacology & Toxicology, Nisell et al, Infusion of Nicotine in the Ventral Tegmental Area or the Nucleus Accumbens of the Rat Differentially Affects Accumbal Dopamine Release, 1994, pp. 348-352.

Synapse, Niseil et al, Systemic Nicotine-Induced Dopamine Release in the Rat Nucleus Accumbens is Regulated by Nicotinic Receptors in the Ventral Tegmental Area, 1994, pp. 36-44.

The New England Journal of Medicine, Henningfield, Nicotine Medications for Smoking Cessation, Nov. 2, 1995, vol. 333, No. 18, pp. 1196-1203.

The New England Journal of Medicine, Hurt et al, A Comparison of Sustained-Release Bupropion and Placebo for Smoking Cessation, Oct. 23, 1997, vol. 337, No. 17, pp. 1195-1202.

* cited by examiner

Rapid Dose-Effect Procedure

Each Component Begins with one Priming
Injection of the Available Dose

Fixed Ratio 30 Schedule of Reinforcement*

| 5' | | 20' | | 20' | | 20' | | 20' | | 5' |

---

* Post-reinforcement timeout = 10 sec

METHODS FOR TREATING DRUG ADDICTION AND IMPROVING ADDICTION-RELATED BEHAVIOR

BACKGROUND OF THE INVENTION

The present invention relates a method of treating addiction to drugs of abuse and modification of behavior associated with drug addiction, especially opioids. More specifically, the present invention is directed to a method of using a carbamate compound alone or in combination with other medications, for the treatment of drug addiction or modification of behavior associated with drug addiction or drug abuse.

DESCRIPTION OF RELATED ART

Substance addiction, such as drug abuse, and the resulting addiction-related behaviors are enormous social and economic problems that continue to grow with devastating consequences.

The addictive liability of drugs of abuse, such as for example, cocaine, nicotine, methamphetamine, morphine, heroin, ethanol, phencyclidine, methylenedioxmethamphetamine or other drugs of abuse has been linked to their pharmacological actions on mesotelencephalic dopamine (DA) reinforcement/reward pathways in the central nervous system (CNS). Dopaminergic transmission within these pathways is modulated by gamma-amino butyric acid (GABA).

Virtually all drugs of abuse, including nicotine, have been shown to acutely increase extracellular dopamine concentrations in the nucleus accumbens of mammals. This increase is clearly associated with the addictive liability of these compounds. Based on this unique biochemical fingerprint, drugs that attenuate or abolish this response may be quite effective for the treatment of substance abuse.

Substance addiction can occur by use of legal and illegal substances. Nicotine, cocaine, amphetamine, methamphetamine, ethanol, heroin, morphine, phencyclidine (PCP), methylenedioxymethamphetamine (MDMA), and other addictive substances are readily available and routinely used by large segments of the United States population. Many drugs of abuse are naturally occurring. For example, cocaine is a naturally occurring nonamphetamine stimulant derived from the leaves of the coca plant, *Erythroylon coca*. Coca leaves contain only about one-half of one percent pure cocaine alkaloid. When chewed, only relatively modest amounts of cocaine are liberated, and gastrointestinal absorption is slow. Certainly, this explains why the practice of chewing coca leaves has never been a public health problem in Latin America. The situation changes sharply with the abuse of the alkaloid itself.

It has been found that addicting drugs such as nicotine, cocaine, amphetamine, methamphetamine, ethanol, heroin, morphine, phencyclidine and methylenedioxymethamphetamine enhance (in some cases directly, in other cases indirectly or even trans-synaptically) dopamine (DA) within the mesotelencephalic reward/reinforcement circuitry of the forebrain, presumably producing the enhanced brain reward that constitutes the drug user's "high."

Alterations in the function of these DA systems have also been implicated in drug craving and in relapse to the drug-taking habit in recovering addicts. For example, cocaine acts on these DA systems by binding to the dopamine transporter (DAT) and preventing DA reuptake into the presynaptic terminal.

There is considerable evidence that nicotine, cocaine, amphetamine, methamphetamine, ethanol, heroin, morphine, phencyclidine, methylenedioxymethamphetamine and other abused drugs' addictive liability is linked to a re-uptake blockade in the central nervous systems' (CNS') reward/reinforcement pathways. For example, cocaine-induced increases in extracellular DA have been linked to its rewarding and craving effects in rodents.

In humans, the pharmacokinetics binding profile of $^{11}$C-cocaine indicates that the uptake of labeled cocaine is directly correlated with the self-reported "high". In addition, human cocaine addicts exposed to cocaine-associated environmental cues experienced increased cocaine craving which is antagonized by the DA receptor antagonist haloperidol. Based upon the presumptive link between cocaine's addictive liability and the DA reward/reinforcement circuitry of the forebrain, many pharmacologic strategies for treating cocaine addiction have been proposed.

In the past, one treatment strategy was to target directly the DAT with a high-affinity cocaine analog, thereby blocking cocaine's binding. Another treatment strategy was to modulate synaptic DA directly by the use of DA agonists or antagonists. Yet another treatment strategy was to modulate synaptic DA, indirectly or trans-synaptically, by specifically targeting a functionally-linked but biochemically different neurotransmitter system.

A number of drugs have been suggested for use in weaning cocaine users from their dependency. Certain therapeutic agents were favored by the "dopamine depletion hypothesis." It is well established that cocaine blocks dopamine reuptake, acutely increasing synaptic dopamine concentrations. However, in the presence of cocaine, synaptic dopamine is metabolized as 3-methoxytyramine and excreted. The synaptic loss of dopamine places demands on the body for increased dopamine synthesis, as evidenced by the increase in tyrosine hydroxylase activity after cocaine administration. When the precursor supplies are exhausted, a dopamine deficiency develops.

The above hypothesis led to the testing of bromocriptine, a dopamine receptor agonist. Another approach was the administration of amantadine, a dopamine releaser. Yet another approach, also based on the dopamine depletion hypothesis, was to provide a precursor for dopamine, such as L-dopa.

Agonists are not preferred therapeutic agents. A given agonist may act on several receptors, or similar receptors on different cells, not just on the particular receptor or cell one desires to stimulate. As tolerance to a drug develops (through changes in the number of receptors and their affinity for the drug), tolerance to the agonist may likewise develop. A particular problem with the agonist bromocriptine, for example, is that it may itself create a drug dependency. Thus, treatment strategies used in the past did not relieve the patient's craving for cocaine. Moreover, by using certain agonists such as bromocriptine, a patient was likely to replace one craving for another.

Another drug that is frequently abused is nicotine. The alkaloid (−)-nicotine is present in cigarettes and other tobacco products that are smoked or chewed. It has been found that nicotine contributes to various diseases, including cancer, heart disease, respiratory disease and other conditions, for which tobacco use is a risk factor, particularly heart disease.

Vigorous campaigns against the use of tobacco or nicotine have taken place, and it is now common knowledge that the cessation of tobacco use brings with it numerous unpleasant withdrawal symptoms, which include irritability, anxiety, restlessness, lack of concentration, lightheadedness, insomnia, tremor, increased hunger and weight gain, and, of course, an intense craving for tobacco.

The addictive liability of nicotine has been linked to the rewarding/reinforcing actions and its effects on DA neurons in the reward pathways of the brain (Nisell et al., 1995; Pontieri, et al., 1996). For example, the acute systemic administration of nicotine, as well as numerous other drugs of abuse, produces an increase in extracellular DA levels in the nucleus accumbens (NACC), an important component of the reward system (Damsma et al., 1989; Di Chiara and Imperato, 1988; Imperato et al., 1986; Nisell et al., 1994a, 1995; Pontieri et al., 1996). Similarly, the infusion of nicotine into the ventral segmental area (VTA) of the rodent produces a significant increase in DA levels in the NACC (Nisell et al., 1994b).

A few pharmaceutical agents have been reported as useful to treat nicotine dependence, including nicotine substitution therapy such as nicotine gum, transdermal nicotine patches, nasal sprays, nicotine inhalers and bupropion, the first normicotinic treatment for smoking cessation (Henningfield, 1995; Hurt, et al., 1997).

Unfortunately, nicotine substitution therapy involves the administration of the nicotine which frequently leads to nicotine withdrawal and subsequent relapse to use of tobacco products. Thus, there is a need for a therapy having a desirable side effect profile, to relieve nicotine withdrawal symptoms, including the long term cravings for nicotine.

Other known addictive substances are narcotic analgesics such as morphine, heroin and other opioids both natural and semisynthetic. Abuse of opioids induce tolerance and dependence. Withdrawal symptoms from the cessation of opioids use vary greatly in intensity depending on numerous factors including the dose of the opioid used, the degree to which the opioid effects on the CNS are continuously exerted, the duration of chronic use, and the rate at which the opioid is removed from the receptors.

These withdrawal symptoms include craving, anxiety, dysphoria, yawning, perspiration, lacrimation, rhinorrhoea, restless and broken sleep, irritability, dilated pupils, aching of bones, back and muscles, piloerection, hot and cold flashes, nausea, vomiting, diarrhea, weight loss, fever, increased blood pressure, pulse and respiratory rate, twitching of muscles and kicking movements of the lower extremities.

Medical complications associated with injection of opioids include a variety of pathological changes in the CNS including degenerative changes in globus pallidus, necrosis of spinal gray matter, transverse myelitis, amblyopia, plexitis, peripheral neuropathy, Parkinsonian syndromes, intellectual impairment, personality changes, and pathological changes in muscles and peripheral nerves. Infections of skin and systemic organs are also quite common including staphylococcal pneumonitis, tuberculosis, endocarditis, septicemia, viral hepatitis, human immunodeficiency virus (HIV), malaria, tetanus and osteomyelitis. The life expectancy of opioid addicts is markedly reduced, due to overdose, drug-related infections, suicide and homicide.

Pharmaceutical agents used in treating opioid dependence include methadone, which is an opioid, and opioid antagonists, primarily naloxone and naltrexone. Clonidine has been shown to suppress some elements of opioid withdrawal but suffers from the side effects of hypotension and sedation, which can be quite extreme. Behavior-modifying psychological treatment and training are frequently adjunctive therapy used in association with pharmaceutical agents. There is a need for a therapy having a more desirable side effect profile, to relieve opioid addiction and withdrawal symptoms.

Ethanol is probably the most frequently used and abused depressant in most cultures and a major cause of morbidity and mortality. Repeated intake of large amounts of ethanol can affect nearly every organ system in the body, particularly the gastrointestinal tract, cardiovascular system, and the central and peripheral nervous systems. Gastrointestinal effects include gastritis, stomach ulcers, duodenal ulcers, liver cirrhosis, and pancreatitis.

Further, there is an increased rate of cancer of the esophagus, stomach and other parts of the gastrointestinal tract with ethanol abuse. Cardiovascular effects include hypertension, cardiomyopathy and other myopathies, significantly elevated levels of triglycerides and low-density lipoprotein cholesterol. These cardiovascular effects contribute to a marked increase risk of heart disease.

Ethanol abuse can manifest in peripheral neuropathy as evidenced by muscular weakness, parathesias, and decreased peripheral sensation. Central nervous system effects include cognitive deficits, severe memory impairment degenerative changes in the cerebellum, and ethanol-induced persisting amnesiac disorder in which the ability to encode new memory is severely impaired. Generally, these effects are related to vitamin deficiencies, particularly the B vitamins.

Individuals with ethanol dependence or addiction exhibit symptoms and physical changes including dyspepsia, nausea, bloating, esophageal varices, hemorrhoids, tremor, unsteady gait, insomnia, erectile dysfunction, decreased testicular size, feminizing effects associated with reduced testosterone levels, spontaneous abortion, and fetal alcohol syndrome. Symptoms associated with ethanol cessation or withdrawal include nausea, vomiting, gastritis, hematemises, dry mouth, puffy blotchy complexion, and peripheral edema.

The generally accepted treatment of ethanol addiction and withdrawal is accomplished by administering a mild tranquilizer such a chlordiazepoxide. Typically, vitamins, particularly the B vitamins, are also administered. Optionally, magnesium sulfate and/or glucose are also administered. Nausea, vomiting and diarrhea are treated symptomatically at the discretion of the attending physician. Disulfuram may also be administered for help in maintaining abstinence. If ethanol is consumed while on disulfuram, acetaldehyde accumulates producing nausea and hypotension. There is a need for a therapy having a more desirable side effect profile, to relieve ethanol addiction and withdrawal symptoms.

Recently, it has been reported that polydrug or combination drug abuse has been increasing at an alarming rate. For example, cocaine and heroin are often abused together in a drug combination known as a "speedballing." Such reported increase is believed to be a result of a synergistic effect that increases the euphoria of the user.

In many instances, drug dealers combine various drugs of abuse to increase the intensity of the "high." This is especially prevalent where the drug user is a regular customer and has built up a tolerance to the drug alone. Most times the drug user is unaware of this dangerous combining.

Phencyclidine, commonly known as PCP, is described as dissociative in action. This means that the mind feels separated from the body. PCP was first used as an anesthetic for surgery in the 1950's. Due to the highly undesirable side effects, such as convulsions and hallucinations, its use was discontinued.

The first reports of the illicit use of PCP originated in the late 1960's. However, due to numerous reports of bad experiences, PCP lost popularity. In the 1970's PCP use re-emerged by itself and in combination with other illicit drugs such as marijuana and cocaine. PCP continues to be an abused substance. Many people after using it once, will not choose to use it again. Others use it consistently and regularly. A numbing effect on pain, both emotional and physical is one reason why others say they use PCP.

PCP is a synthetic substance that can be in the form of a pill, powder or liquid suspension. It can be smoked, snorted, orally ingested or intravenously administered. The short-term effects can last for hours or days and include rapid breathing, increased blood pressure and heart rate, increased temperature, profuse sweating, bizarre postures and muscle jerking. Higher doses can cause vomiting, blurred vision, convulsions and coma.

The long-term effects of PCP include flashbacks, speech problems, loss of memory, anxiety, depression and social withdrawal. Frequent users report the need to increase intake to maintain a 'high'. There is no known accepted treatment for PCP abuse.

Methylenedioxymethamphetamine (MDMA), commonly known as "ecstacy," is a synthetic psychoactive drug possessing stimulant and hallucinogenic properties. MDMA was first synthesized in 1912 as a possible appetite suppressant. Illicit use of MDMA did not become popular until the late 1980's.

MDMA is usually taken orally and its effects can last from four to six hours. Users say that it produces profoundly positive feelings and extreme relaxation. MDMA is also said to suppress the need to eat, drink or sleep. Consequently, MDMA use sometimes results in severe dehydration or exhaustion.

MDMA users may encounter problems similar to those of amphetamine and cocaine users, which includes addiction. In addition, MDMA can cause confusion, depression, sleep problems, anxiety, and paranoia. Physical effects of MDMA use include muscle tension, involuntary teeth clenching, nausea, blurred vision, faintness and chills or sweating.

The effects of long term MDMA use are just beginning to undergo scientific analysis. The National Institute of Mental Health conducted a study of habitual MDMA users in 1998 that revealed damage to the neurons of the brain that transmit serotonin. Serotonin is an important biochemical involved in a variety of critical functions including learning, sleep and integration of emotion. The results of the study indicate that MDMA users are at risk of developing permanent brain damage that may manifest itself in depression, anxiety, memory loss and other neuropsychotic disorders. There is no known and accepted treatment for MDMA abuse.

Accordingly, there is a need in the treatment of addiction to drugs of abuse to provide new methods which can relieve a patient's craving by changing the pharmacological actions of drugs of abuse in the central nervous system. There is also a need to provide new methods to treat combination drug abuse.

SUMMARY OF THE INVENTION

The present invention is directed to a method of treating drug addiction comprising the administration of a therapeutically effective amount of a compound having structural Formula (1) or a pharmaceutically acceptable salt or ester thereof, to a mammal in need of treatment:

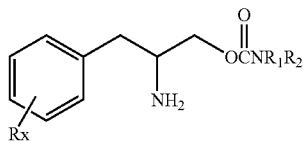

(I)

wherein,
R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

In another embodiment, the present invention provides, a method of improving behavior associated with addiction to drugs of abuse in a subject, comprising the step of the administration, to a subject in need of such treatment, of a therapeutically effective amount a compound of the Formula (1) or a pharmaceutically acceptable salt or ester thereof.

In further embodiment, the present invention provides a method of ameliorating or eliminating effects of addiction to a drug of abuse in a subject, comprising the step of the administration, to a subject in need of such treatment, of a therapeutically effective amount a compound of the Formula (1) or a pharmaceutically acceptable salt or ester thereof.

In additional embodiment, the present invention is directed to pharmaceutical composition for treating drug addiction comprising a therapeutically effective amount a compound of the Formula (1) or a pharmaceutically acceptable salt or ester thereof.

In another embodiment, the present invention provides a pharmaceutical composition for improving behavior associated with addiction to drugs of abuse in a subject, comprising a therapeutically effective amount a compound of the Formula (1) or a pharmaceutically acceptable salt or ester thereof.

In further embodiment, the present invention provides a pharmaceutical composition for ameliorating or eliminating effects of addiction to a drug of abuse in a subject, comprising a therapeutically effective amount a compound of the Formula (1) or a pharmaceutically acceptable salt or ester thereof.

The compound having structural Formula (1) is an enantiomer substantially free of other enantiomers or an enantiomeric mixture wherein one enantiomer of the compound having structural Formula (1) predominates. One enantiomer predominates to the extent of about 90% or greater, and preferably about 98% or greater.

The enantiomer is (S) or (L) enantiomer as represented by Structural Formula (1a) or (R) or (D) enantiomer, as represented by Structural Formula (1b):

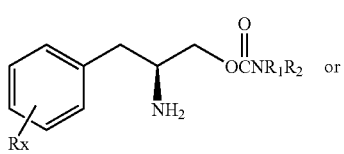

(1a)

or

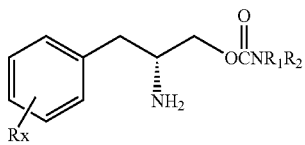
(1b)

Preferably, Rx, R1 and R2 are all selected from hydrogen and x is 1, which are shown in the following formula:

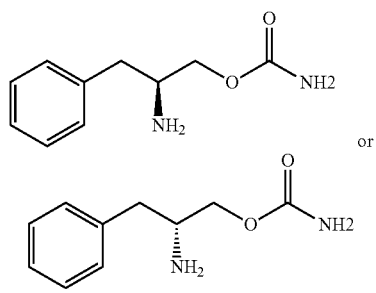

Embodiments of the invention include a method for using the enantiomer of Formula 1 substantially free of other enantiomers that is the enantiomer of Formula 1b or an enantiomeric mixture wherein the enantiomer of Formula 1b predominates. (note: in the structural formula of Formula 1b below the amino group attached to the beta carbon projects into the plane of the paper. This is the dextrorotary (D) enantiomer that is of absolute configuration (R)

Drugs of abuse are selected from the group consisting of nicotine, cocaine, opioids, amphetamine, methamphetamine, ethanol, heroin, morphine, phencyclidine (PCP), methylenedioxymethamphetamine (MDMA), and other addictive substances.

BRIEF DESCRIPTION OF THE DRAWING

The drawing is a diagram of the Rapid Assessment Procedure in Example 3.

DETAILED DESCRIPTION OF THE EMBODIMENT

These and other objects of the invention will be more fully understood from the following description of the invention, and the claims appended hereto.

The present invention is directed to a method of treating drug addiction comprising the administration of a therapeutically effective amount of a compound having structural Formula (1) or enantiomers, diastereomers, racemates or mixtures thereof, or hydrates, solvates and pharmaceutically acceptable salts, esters and amides thereof, to a mammal in need of treatment:

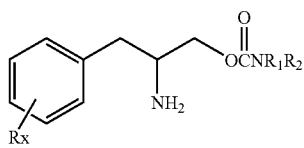
(I)

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

The present method also includes the use of a compound selected from the group consisting Formula 1a or 1b, or enantiomers, diastereomers, racemates or mixtures thereof, or hydrates, solvates and pharmaceutically acceptable salts, esters and amides thereof:

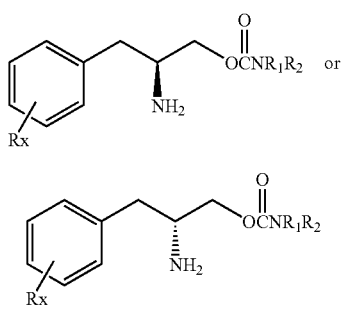
(1a)

(1b)

wherein Rx, R1 and R2 are the same as defined above.

The present method also preferably includes the use of the D (or dextrorotary) enantiomer (of absolute configuration R) selected from the group consisting of Formula 1 or an enantiomeric mixture thereof. In the structural formula of Formula 1b, the amino group attached to the beta carbon projects into the plane of the paper. This is the dextrorotary (D) enantiomer that is of absolute configuration (R)

Preferably, in the Structural Formula 1, Rx, R1 and R2 are hydrogen and x is 1 as represented by following Structural Formula:

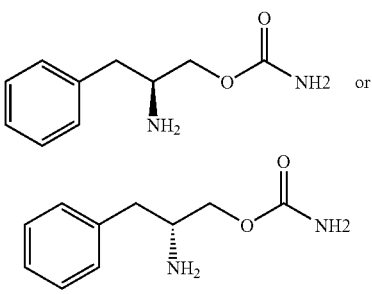

O-carbamoyl-(D)-phenylalaminol is also named (R)-(beta-amino-benzenepropyl) carbamate monohydrochloric acid. For enantiomeric mixtures wherein O-carbamoyl-(D)- phenylalaminol predominates, preferably, to the extent of about 90% or greater, and more preferably about 98% or greater.

The compounds of Formula 1 can be synthesized by methods known to a skilled person in the art. Some reaction schemes for synthesizing compounds of Formula (1) have been described in published; U.S. Pat. Nos. 5,705,640, 5,756, 817, 5,955,499, and 6,140,532. Details of the above reactions schemes as well as representative examples on the preparation of specific compounds have been described in published; U.S. Pat. Nos. 5,705,640, 5,756,817, 5,955,499, 6,140,532, all incorporated herein by reference in their entirety.

The salts and esters of the compounds of Formula (1) can be produced by treating the compound with an acid (HX) in suitable solvent or by means well known to those of skill in the art.

From Structural Formula 1, it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

The present invention is based in part on the discovery that phenylalkylamino carbamates of Formula 1 discussed above have novel and unique pharmacological properties. These compounds have been shown in numerous animal models to have the ability to treat addiction to drugs of abuse and modification of behavior associated with addiction to drugs of abuse Although the precise mechanism of action is not completely understood it is known that these compounds do not work by the same mechanisms as most other known treatments for addiction to drugs of abuse. For these reasons the compounds of Formula 1 are especially suitable for use as sole or adjunctive treatment for addiction to drugs of abuse and modification of behavior associated with addiction to drugs of abuse.

Thus, these compounds can be safely used alone or in combination with other useful medications to provide enhanced efficacy and reduced side effects because of the smaller doses of each drug that can be used.

In one aspect, this invention relates to methods to treat subjects suffering from addiction to drugs of abuse; the method comprising delivering to the subject a therapeutically effective amount of one or more of the carbamate compounds of the invention or a pharmaceutically acceptable salt or ester thereof and a pharmaceutically acceptable carrier, diluent or excipient.

In one aspect, this invention also provides a method for diminishing, inhibiting or eliminating the rewarding/incentive effects of drugs of abuse in a subject suffering from addiction to drugs which comprises administering to the subject an effective amount of carbamate compounds of the invention to diminish, inhibit or eliminate said rewarding/incentive effects.

Drugs of abuse are selected from the group consisting of nicotine, cocaine, amphetamine, methamphetamine, ethanol, heroin, morphine, phencyclidine (PCP), methylenedioxymethamphetamine (MDMA), and other addictive substances.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject", refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician.

The term "pharmaceutically acceptable salts or esters" shall mean non-toxic salts or esters of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patient's present clinical condition or prognosis could benefit from the administration of one or more compounds of Formula (1)

alone or in combination with another therapeutic intervention including but not limited to another medication. The terms "patient" is mean any mammal including but not limited to human beings including a human patient, both male and female and non-human primates, as well as experimental animals such as rabbits, rats, and mice, and other animals.

The term "treating" or "treatment" as used herein, refers to any indicia of success in the prevention or amelioration of an injury, pathology or condition of addiction to drugs of abuse and modification of behavior associated with addiction to drugs of abuse, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention for treatment of any form of addiction to drugs of abuse in both males and females. In some instances, treatment with the compounds of the present invention will done in combination with other compounds to prevent, inhibit, or arrest the progression of the addiction to drugs of abuse.

The term "therapeutic effect" as used herein, refers to the effective improvement in or reduction of symptoms of addiction to drugs of abuse. The term "a therapeutically effective amount" as used herein means a sufficient amount of one or more of the compounds of the invention to produce a therapeutic effect, as defined above, in a subject or patient in need of such neuroprotection treatment.

Methods are known in the art for determining therapeutically and prophylactically effective doses for the instant pharmaceutical composition. For example the compound can be employed at a daily dose in the range of about 0.1 mg to 400 mg usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (1) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (1) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents. In these embodiments, the present invention provides methods to treat addiction to drugs of abuse and modification of behavior associated with addiction to drugs of abuse in a patient. The method includes the step of; administering to a patient in need of treatment, an effective amount of one of the carbamate compounds disclosed herein in combination with an effective amount of one or more other compounds or therapeutic agents.

It is understood that substituents and substitution patterns on the compounds of the present invention can be selected by one of ordinary skill in the art to provide compounds that are chemically stable and that can be readily synthesized by techniques known in the art as well as the methods provided herein.

Representative 2-phenyl-1,2-ethanediol monocarbomates and dicarbamates include, for example, the following compounds

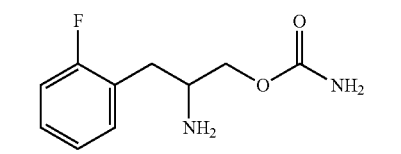

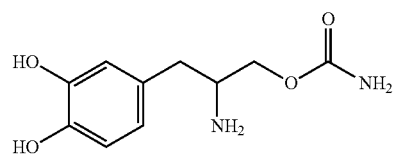

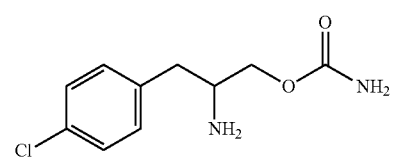

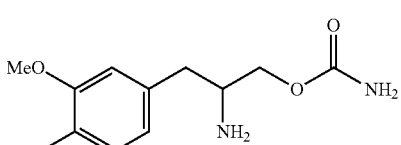

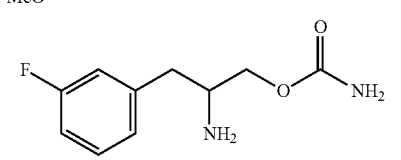

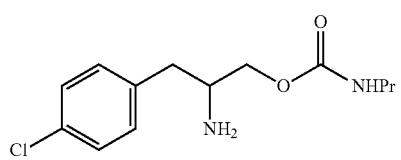

-continued

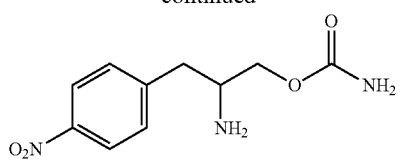

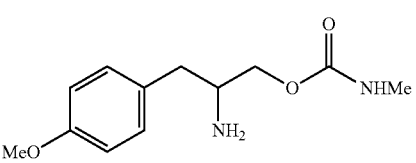

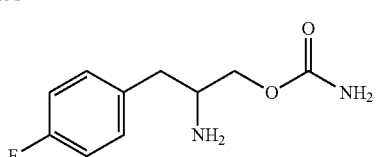

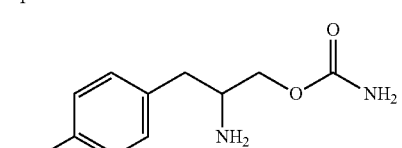

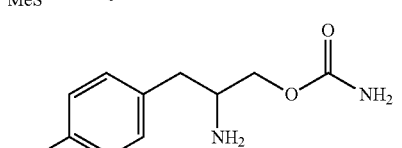

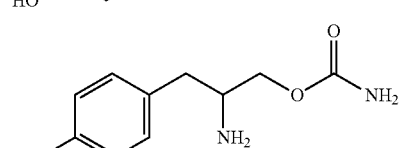

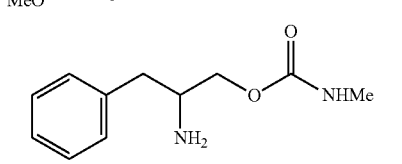

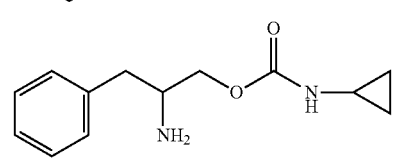

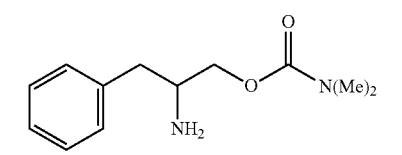

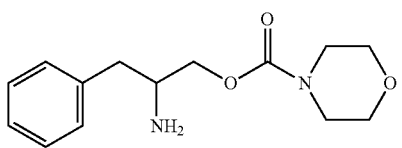

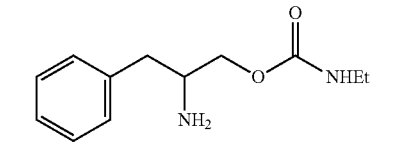

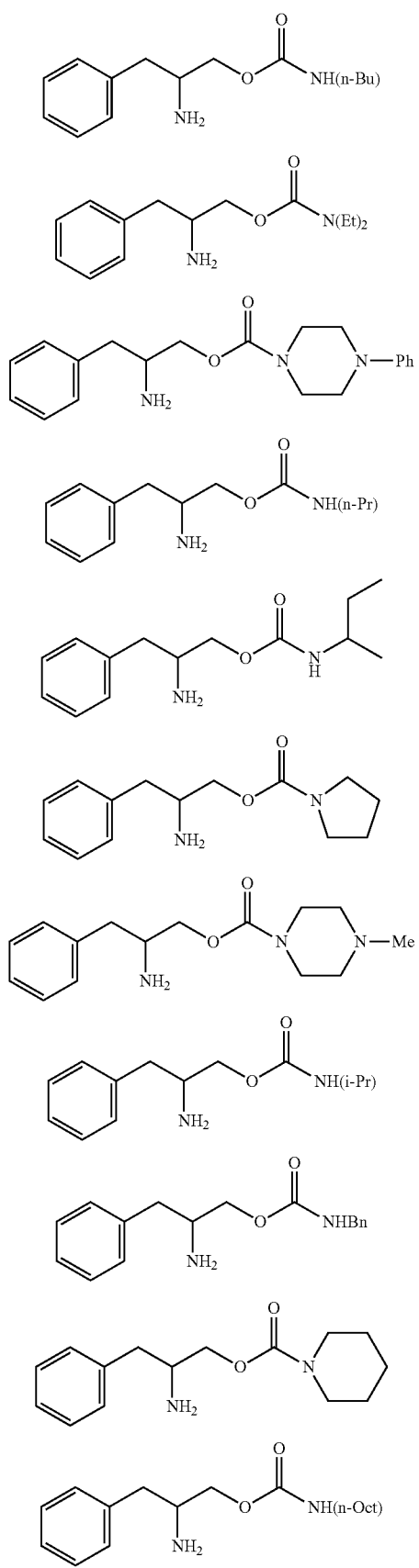
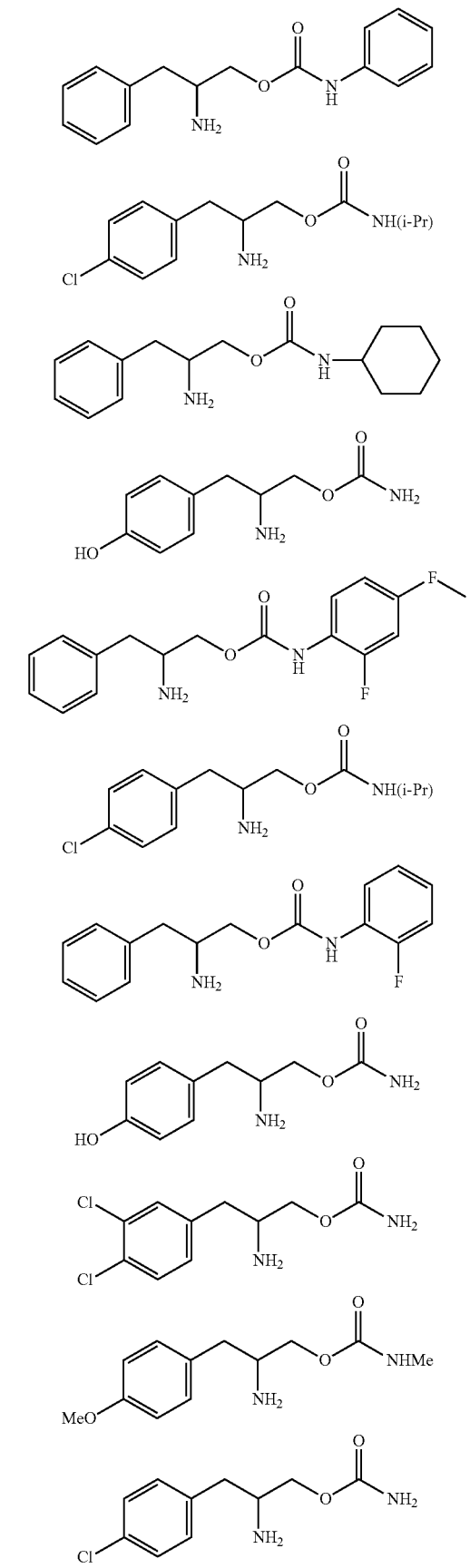

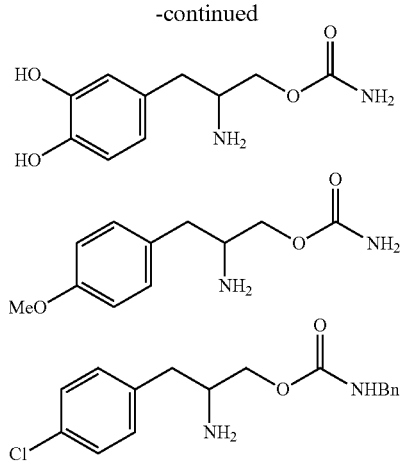

The present invention includes the use of isolated enantiomers of Formula 1. In one preferred embodiment, a pharmaceutical composition comprising the isolated S-enantiomer of Formula 1 is used to provide drug abuse addiction treatment in a subject. In another preferred embodiment, a pharmaceutical composition comprising the isolated R-enantiomer of Formula 1 is used to provide drug abuse addiction treatment a subject.

The present invention also includes the use of mixtures of enantiomers of Formula 1. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1. A carbamate enantiomer of Formula 1 contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula 1 as pharmaceuticals. The carbamate compounds are formulated as pharmaceuticals to provide adjuvant antidepressant action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solution, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts and esters refer to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (1). More than one crystal form of an enantiomer of Formula 1 can exist and as such are also included in the present invention.

A pharmaceutical composition of the invention can optionally contain, in addition to a carbamate compound, at least one other therapeutic agent useful in the treatment of addiction to drugs of abuse. For example the carbamate compounds of Formula 1 can be combined physically with other addiction treatments in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms: Parenteral Medications*. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing adjuvant antidepressant action in a mammal using carbamate compounds. The amount of the carbamate compound necessary to reduce or treat addiction to drugs abuse is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent that is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the carbamate compounds can include repeated doses within a prolonged treatment regimen that will yield clinically significant results to treat addiction to drugs of abuse. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg. to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1/mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment of addiction to drugs of abuse. After a pharmaceutical composition comprising one or more carbamate compounds of this invention, with the possible addition of one or more other compounds of therapeutic benefit, has been formulated in a suitable carrier, it can be placed in an appropriate container and labeled for providing drug abuse addiction treatment. Additionally, another pharmaceutical comprising at least one other therapeutic agent useful in the drug abuse addiction treatment can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

A better understanding of the present invention may be obtained in light of the following examples that are set forth to illustrate, but are not to be construed to limit, the present invention.

EXAMPLE 1

The test compound (O-carbamoyl-(D)-phenylalaminol) substituted fully for the discriminative stimulus effects produced by 10 mg/kg of cocaine (ED50=37.43 mg/kg). Response rate was decreased to 41% of control following 100 mg/kg of test compound.

(Methods)

Test compound was tested for its ability to substitute for the discriminative stimulus effects of cocaine (10 mg/kg) in rats.

Six male Sprague-Dawley rats were trained to discriminate cocaine (10 mg/kg) from saline using a two-lever choice methodology. Food was available as a reinforcer under a fixed ratio 10 schedule when responding occurred on the injection appropriate lever. All tests occurred in standard, commercially available chambers (Coulbourn Instruments), using 45 mg food pellets (Bioserve) as reinforcers.

Training sessions occurred in a double alternating fashion, and tests were conducted between pairs of identical training sessions (i.e., between either two saline or two cocaine training sessions). Tests occurred only if, in the two preceding training sessions, subjects met the criteria of emitting 85% of responses on the injection correct lever for both the first reinforcer (first fixed ratio) and the total session. Test sessions lasted for twenty minutes, or until twenty reinforcers had been obtained. Doses of the test compound for which fewer, than three rats completed the first fixed ratio were not considered in the characterization of discriminative stimulus effects.

Intraperitoneal injections (1 ml/kg) of test compound, or its vehicle (0.9% saline), occurred 60 minutes prior to the start of the test session. A starting dose for test compound of 2.5 mg/kg was determined based upon data supplied by the project officer, and a dose range of 2.5 to 100 mg/kg was examined. This range included doses that were inactive to those that had biological activity as evidenced by full substitution.

(Results)

Total session. Test compound fully substituted for the discriminative stimulus effects produced by 10 mg/kg of cocaine. An ED50 of 37.43 mg/kg was determined based upon a linear regression against log 10 doses from 10 to 100 mg/kg. Response rate was decreased to 41% of vehicle control following 100 mg/kg test compound. A one-way, repeated measures analysis of variance conducted on response rate for the total session (for the 4 rats receiving all doses) indicated a significant overall effect $F(6,18)=3.38$, $p=0.021$; planned comparisons (a priori contrast) against vehicle control showed a significant difference for the 100 mg/kg dose (all $ps<0.05$ denoted on FIG. 1 with an asterisk).

First reinforcer. The results for the first reinforcer measure were in general accordance with the total session data. An ED50 of 37.45 mg/kg was determined based upon a linear regression against log 10 doses from 10 to 100 mg/kg. Response rate was decreased to 37% of vehicle control following 100 mg/kg test compound. A one-way, repeated measures analysis of variance conducted on response rate for the first reinforcer (for the 4 rats receiving all doses) indicated a significant overall effect $F(6,18)=3.82$, $p=0.012$; planned comparisons (a priori contrast) against vehicle control showed a significant difference for the 100 mg/kg dose.

EXAMPLE 2

Test compound (O-carbamoyl-(D)-phenylalaminol) (0.1-18 mg/kg) was evaluated for its ability to substitute for cocaine in four monkeys trained to discriminate cocaine (0.40 mg/kg) from saline in a drug discrimination procedure. Test compound produced dose-dependent and complete substitution for cocaine in all four monkeys. Across the dose range tested, Test compound increased response rates in two monkeys, and cocaine also increased response rates in these two monkeys. In a third monkey, neither test compound nor cocaine altered response rates, and in a fourth monkey, both test compound and cocaine decreased response rates. Test compound also did not produce overt behavioral effects across the dose-range tested. These findings suggest that test compound produces cocaine-like behavioral effects in rhesus monkeys and is approximately 20-fold less potent than cocaine.

(Methods)

Subjects: The subjects were four male rhesus monkeys (*Macaca mulatta*) each weighing 7.0-8.0 kg. Each monkey was maintained on a diet of 7-12 monkey biscuits (Purina Monkey Chow Jumbo #5037) and one piece of fresh fruit per day. During the week, all food was delivered after the experimental session, whereas on weekends, food was delivered between 9 a.m. and noon. Water was freely available at all times. The room in which the monkeys were housed was maintained on a 12-hr light/dark cycle, with lights on from 7 a.m. to 7 p.m.

Monkeys had visual, auditory and olfactory contact with other monkeys throughout the study. Operant food self-administration procedures provide an opportunity for environmental manipulation and enrichment.

Apparatus: Each monkey was housed individually in a well-ventilated, stainless steel chamber (56×71×69 cm). The home cages of all monkeys were modified to include an operant panel (28×28 cm) mounted on the front wall. Three square translucent response keys (6.4×6.4 cm) were arranged 2.54 cm apart in a horizontal row 3.2 cm from the top of the operant panel. Each key could be transilluminated by red or green stimulus lights (Superbright LED'S). In addition, the operant panel supported an externally mounted pellet dispenser (Gerbrands, Model G53 10, Arlington, Mass.) that delivered 1 gm fruit-flavored food pellets (Precision Primate Pellets Formula L/I Banana Flavor, P. J. Noyes Co., Lancaster, N.H.) to a food receptacle mounted on the cage beneath the operant response panel. Operation of the operant panels and data collection were accomplished with IBM-compatible computers and interface systems (MedAssociates; St. Albans, Vt.) located in a separate room.

Discrimination Training: Discrimination training was conducted 5 days per week during daily sessions composed of multiple cycles. Each cycle consisted of a 15-min time-out period followed by a 5-min response period. During the time-out, all stimulus lights were off, and responding had no scheduled consequences. During the response period, the right and left response keys were transilluminated red or green, and monkeys could earn up to 10 food pellets by responding under a FR 30 schedule of food presentation. For all four monkeys in this study, the left key was illuminated green, and the right key was illuminated red. The center key was not illuminated at any time, and responding on the center key had no scheduled consequences. If all available food pellets were delivered before the end of the 5-min response period, the stimulus lights transilluminating the response keys were turned off, and responding had no scheduled consequences for the remainder of the 5-min period.

On training days, monkeys were given an i.m. injection of either saline or 0.40 mg/kg cocaine 5-min after the beginning of each time-out period (i.e., 10 min before the response period). Following the administration of saline, responding on only the green key (the saline-appropriate key) produced food, whereas following administration of 0.40 mg/kg cocaine, only responding on the red key (the drug-appropriate key) produced food. Responses on the inappropriate key reset the FR requirement on the appropriate key. Sessions consisted of 1 to 5 cycles, and if the training dose of cocaine was administered, it was administered only during the last cycle. Thus, training days consisted of 0 to 5 saline cycles followed by 0 to 1 drug cycles.

During each response period, 3 dependent variables were determined using the following equations.

1) Percent injection-appropriate responding prior to delivery of the first reinforcer.

$$\frac{\text{Injection-Appropriate Responses Emitted prior to 1st Reinforcer}}{\text{Total Responses Emitted Prior to Delivery of 1st Reinforcer}} \times 100$$

2) Percent injection-appropriate responding for the entire response period.

$$\frac{\text{Injection-Appropriate Responses Emitted During Response Period}}{\text{Total Responses Emitted During Response Period}} \times 100$$

3) Response Rate $$\frac{\text{Total Response Emitted During Response Period}}{\text{Total Response Keys Transilluminated}} \times 100$$

Monkeys were considered to have acquired cocaine discrimination when the following three criteria were met for 7 of 8 consecutive training sessions: 1) the percent injection-appropriate responding prior to delivery of the first reinforcer was greater than or equal to 80% for all cycles; 2) the percent injection-appropriate responding for the entire cycle was greater than or equal to 90% for all cycles; 3) response rates during saline training cycles were greater than 0.5 responses per second.

Discrimination Testing: Once monkeys met criterion levels of cocaine discrimination, testing began. Test sessions were identical to training sessions except that 1) responding on either key produced food and 2) test compound (0.1-18 mg/kg) was administered using a substitution protocol. In the substitution protocol, Test compound was administered alone, instead of either saline or cocaine, using a cumulative dosing procedure. Monkeys received an injection of test compound at the beginning of each cycle of a multiple cycle session, and each dose increased the total dose by ¼ or ½ log units.

Test sessions were conducted only if the three criteria listed above under "Criteria for Discrimination" were met during the training day immediately preceding the test day. Mean data from saline and drug cycles during the training day immediately preceding the initial test day served as the control data for the subsequent test day. If responding did not meet criterion levels of discrimination performance, then training was continued until criterion levels of performance were obtained for at least two consecutive days.

Data Analysis: Individual subject graphs of the Percent Cocaine-Appropriate Responding (for the entire response period) and the Response Rate were plotted as a function of the dose of test compound (log scale). Control data from saline and cocaine training cycles were also included in each graph for comparison. Test compound was considered to have generalized to cocaine if some dose of test compound produced at least 90% cocaine-appropriate responding. ED50 values were defined as the dose of test compound that produced 50% cocaine-appropriate responding, and ED50 values were calculated by linear interpolation in all monkeys in which test compound dose-dependently produced ≧50% cocaine-appropriate responding.

Drugs: Cocaine hydrochloride was dissolved in sterile saline. Test compound was dissolved in distilled water.

(Results)

During the training days preceding test days, monkeys responded almost exclusively on the saline key during saline cycles (mean saline-appropriate responding=98.75±1.25%) and exclusively on the cocaine key during cocaine cycles. Mean response rates were 1.79 (±0.44) and 2.58 (±0.67) responses/sec during saline and drug training cycles, respectively. Relative to saline control response rates, the training dose of cocaine increased response rates in monkeys 92N012 and L958, had no effect on response rates in monkey 186F, and decreased response rates in monkey 153F.

Test compound (0.1-18 mg/kg) substituted completely for the cocaine training stimulus in all four monkeys. In all four monkeys, doses of test compound that substituted for cocaine produced effects on response rates similar to those produced by the training dose of cocaine. Specifically, test compound increased response rates in monkeys 92N012, had no effect on response rates in monkey 186F, and decreased response rates in monkey 153F. Across the dose-range tested, test compound did not produce noticeable overt behavioral effects in any of the monkeys.

TABLE 1

ED50 values (mg/kg) for test compound in producing cocaine-appropriate responding in individual monkeys.

| Monkey | ED50 |
| --- | --- |
| 92N012 | 1.8 |
| 153F | 5.6 |
| L958 | 5.6 |
| 186F | 13.4 |

These findings suggest that test compound produces cocaine-like behavioral effects in rhesus monkeys and is approximately 20-fold less potent than cocaine.

EXAMPLE 3

The test compound (O-carbamoyl-(D)-phenylalaminol) was tested for the effects on cocaine self-administration in rhesus monkeys. Rhesus monkeys were trained to self-administer cocaine (0.032 mg/kg/inj, i.v.) and 1 g banana-flavored food pellets during 2-hr experimental sessions in the Rapid Assessment Procedure. Each session consisted of four 20-min components of drug availability (100-min), each separated by a 5-min timeout period. The four components of drug availability were preceded and followed by 9 min components of food availability. During training, unit doses of cocaine were varied across components of the session (0.001-0.03 or 0.01-0.32 mg/kg/inj) to provide full dose effect curves for cocaine self-administration. The position and slope of the dose-effect curve varied among monkeys and, generally, was represented by an inverted-U shape function characteristic for cocaine self-administration under fixed-ratio schedules. In some sessions, the unit dose of cocaine at the peak of the dose-effect curve for i.v. self-administration (0.0032 or 0.032 mg/kg/inj) was kept constant across components of the session. After baseline cocaine dose-effect curves and the effects of peak dose availability throughout the session were stable, experiments with test compound were begun.

Dose-ranging Studies with Test Compound

Two types of cocaine self-administration experiments were conducted to evaluate pretreatment with test compound: (1) test compound dose-ranging studies and (2) effects of a single dose of test compound on cocaine dose-effect curves. In initial dose-ranging experiments, test compound was studied in individual monkeys by administering i.m. doses of 10-32 mg/kg 30-min before the session. Averaged data for the group of monkeys show that 18 or 32 mg/kg test compound markedly decreased self-administration behavior maintained by the peak unit dose of i.v. cocaine without consistently disrupting food-maintained behavior in individual monkeys. The lower dose of test compound (10 mg/kg) did not have consistent effects on cocaine self-administration.

Acute Effects of Test Compound on the Cocaine Dose-effect Curve.

Next, the Rapid Assessment Procedure was used to evaluate the effects of a single i.m. dose of test compound on self-administration of a range of unit doses of cocaine within a single experimental session. Averaged data for the group of monkeys show that i.m. pretreatment with 32 mg/kg test compound decreased cocaine self-administration behavior during availability of unit doses of i.v. cocaine ranging from 0.032-0.32 mg/kg and either increased or did not change response rates during the availability of saline or lower unit doses of cocaine. During rapid assessment studies, food-maintained behavior was disrupted in two monkeys and unaffected in the remaining two monkeys, resulting in a >50% decrease in averaged response rates prior to or following sessions of cocaine self-administration. These data indicate that test compound may reduce self-administration of higher i.v. unit doses of cocaine without consistent effects on food-maintained behavior.

(Methods)

Subjects. Five male rhesus monkeys (*Macaca mulatta*), 89B013, 96D155, 97D105, RQ22 15, and 93N082, were trained to respond for the delivery of 1-g banana pellets under a program of gradually increasing values of a fixed-ratio (FR) schedule until performance was maintained under the terminal FR 30 response schedule. Then, a double-lumen intravenous catheter was surgically implanted under aseptic-conditions in each monkey. Subsequently, monkeys were trained to respond for cocaine (see below). All monkeys were maintained under identical housing conditions as specified under contract DA-7-8073. Individual monkeys had visual, auditory, and olfactory contact with other monkeys, and several types of enrichment devices were provided in the home chamber.

Apparatus. All experimental equipment was identical to that used in our previously described drug self-administration studies. Briefly, each monkey was housed individually in a well-ventilated stainless steel chamber (64×64×79 cm). The home cages of all monkeys were modified to include an operant panel (28×28 cm) mounted on the front wall and fitted with response keys that could be trans-illuminated by red or green stimulus lights (LEDs). The operant panel also supported an externally-mounted pellet dispenser (Gerbrands, Model G5210) that delivered 1 gm fruit-flavored food pellets (P. J. Noyes Co., Lancaster, N.H.) to a food receptacle mounted on the cage beneath the operant response panel. Two syringe pumps (Model B5P-IE, Braintree Scientific, Braintree, Mass.; or Model 980210, Harvard Apparatus, South Natick, Mass.) were mounted above each cage for delivery of saline or drug solutions through the double-lumen intravenous catheters. Operation of the operant panels and data collection were accomplished with an LBM-compatible computer supplied by Med Associates, Inc., and located in an adjacent room. The experimental control hardware was supplied by Med Associates, Inc., and was controlled by customized-software written in MedState Notation.

Test sessions. A diagram of the Rapid Assessment Procedure is shown in the drawing. Test sessions occurred twice daily beginning at 11 a.m. and 3 p.m. At each time, the room lights were extinguished and an illuminated response panel was activated to begin a two-hour session (see the diagram shown in the drawing). Each session consisted of six response components separated by five-min timeout periods. During the first and last components (the food components), 1 g banana flavored food pellets were available under an FR 30; TO 10 sec schedule for five minutes. During the second, third, fourth, and fifth components (the drug components) intravenous injections of cocaine or saline were available under an FR 30; TO 10 sec schedule for twenty minutes. The response key was illuminated with red lights during the food components and with green lights during the drug components. During the 10-sec timeout following each reinforcer delivery, the response key was illuminated with yellow lights. During inter-component timeout periods, the lights illuminating the response key were turned off, and responding had no scheduled consequences. Each twenty-min drug self-administration component was preceded by illumination of the yellow light for 10 sec together with the non-contingent delivery of a single "priming" injection of the dose of cocaine or saline that was available during the ensuing test component.

Varying the unit dose of cocaine during drug self-administration components. The unit dose of cocaine available for self-administration remained constant across components during sessions in which the peak i.v. dose of cocaine was available for self-administration and varied across components during rapid assessment of the dose-effect function for cocaine self-administration. For sessions involving rapid assessment, the unit dose available during each drug component was determined by 1) the duration of each infusion and the resulting volume of each infusion, and 2) the concentration of drug in the syringe. The different infusion durations resulted in different infusion volumes as follows: 32 ul in 0.32 sec; 100 ul in 1 sec; 320 ul in 3.2 sec; 1000 ul in 10 sec. The actual unit dose associated with each infusion duration/infusion volume depended on the concentration of cocaine in the syringe. For example, a concentration of cocaine of 0.032 mg/kg/100 ul was used for cocaine injections in the following dose range: 0.01 mg/kg in 32 ul; 0.032 mg/kg in 100 ul; 0.10 mg/kg in 320 ul; 0.32 mg/kg in 1000 ul. When different unit doses of cocaine were available in different components of a single test session, the dose of cocaine was always incremented in an ascending order. In addition, the range of doses studied during different sessions was varied so that overlapping cocaine dose-effect curves were determined. For example, a range of 0.001, 0.0032, 0.01, and 0.032 mg/kg/inj cocaine might be studied during the four drug components of one session, and a range of 0.01, 0.032, 0.10 and 0.32 mg/kg/inj might be studied during the four components of another test session.

Training procedure and duration of training. Training under the rapid assessment procedure began with sessions that only included the two food components. During drug components, all lights were extinguished and the subjects effectively were in a timeout period. This initial training continued until responding for food pellets was reliably maintained under the FR 30 (FR 10 for 93N082) schedule. After food-maintained performance was stable, the drug components were added to the session and cocaine self-administration training was initiated. All subjects were trained to respond for cocaine under the FR 30-response schedule used for food-maintained behavior (FR 10-response schedule for 93N082). Subsequent training included the following phases:

(1) Initially, all monkeys were trained to self-administer 0.032 mg/kg/inj cocaine during the four drug components without noncontingent "priming" injections of cocaine and without restriction on the number of injections that could be self-administered in each component. Extinction training also was begun by substituting saline for cocaine during the entire session. Saline substitution was introduced on a double alternation basis (two session of cocaine self-administration followed by two sessions of saline availability) or even more frequently if satisfactory extinction of saline-maintained responding was not apparent.

(2) After reliable extinction was evident, the training procedure was modified to incorporate noncontingent priming injections at the beginning of each drug component. Initially, the priming injection was 0.032 mg/kg cocaine at the start of each component during which cocaine was available and 100 ul saline at the start of each component during which saline was available. Generally, extinction behavior was not greatly disrupted by the introduction of priming injections.

(3) After several weeks of exposure to priming injections, the procedure was further modified to present various unit doses of cocaine during the self-administration components of the session. In some sessions, the syringe was filled with a cocaine solution adjusted to deliver 0.032 mg/kg/inj and the pump durations and injection volumes were varied so as to deliver injections of 0.01, 0.032, 0.1, and 0.32 mg/kg during successive components of the session (High Range). In other sessions, the syringe was filled with a cocaine solution adjusted to deliver 0.0032 mg/kg/inj and the pump durations and injection volumes were varied so as to deliver injections of 0.001, 0.0032, 0.01 and 0.032 mg/kg/inj during successive components of the session (Low Range). During saline extinction sessions, the syringe was filled with saline and increasing volumes of saline (32 ul-11000 ul) were delivered across successive session components.

At the same time that variable doses of cocaine were introduced during training, the magnitude of the non-contingent priming injection also was changed so that the delivered dose, rather than being constant (0.032 mg/kg), was the same as the unit dose available for self-administration during the immediately following component. After these modifications, training continued without further changes according to the schedule shown below.

Experiments with test compound were conducted by administering selected doses intramuscularly 30-min prior to experimental sessions. Provided that data from immediately previous sessions were comparable to control values for cocaine self-administration and saline extinction, test sessions generally occurred, on Tuesdays or Fridays. When data from sessions immediately prior to scheduled test sessions varied appreciably from control values for cocaine self-administration or saline extinction (i.e. a decrease of 50% or more in response rate or number of infusions at one or more control doses of cocaine), evaluation of the test compound was suspended until consistent values again were obtained.

| Dose Range Schedule for the Rapid Dose Effect Procedure | | | | | | |
|---|---|---|---|---|---|---|
| Mon | Tues | Weds | Thurs | Fri | Sat | Sun |
| A.M. | | | | | | |
| Sal | Low | Peak | Sal | High | Sal | High |
| P.M. | | | | | | |
| Sal | Peak | Peak | Sal | Peak | Peak | Peak |

Data Analysis. The principal dependent variables for these studies were the number of reinforcers (food pellets or injections) delivered during each component of the test session and response rate (response key presses per second). Response rates were calculated by dividing the number of responses in the component of the session by the number of seconds in the component, excluding the elapsed time during the 10-sec timeouts following each delivery. For individual monkeys, the number of reinforcers per component was very closely correlated to response rates under this procedure because monkeys were responding under a fixed ratio schedule, the duration of the post-reinforcer timeout period was short (10 sec), and, following training, the number of reinforcers per component was not limited.

Drugs. Cocaine HCl and test compound were dissolved in sterile saline. Cocaine was available for intravenous self-administration and test compound was injected intramuscularly 30-min preceding the start of the session.

(Results)

Dose-Ranging Studies with Test Compound

Cocaine self-administration. When a peak unit dose of cocaine (0.0032 or 0.032 mg/kg/inj) was available for i.v. self-administration, pre-session administration of test compound had effects on responding that varied in relation to i.m. pretreatment dose. Averaged for the group of monkeys, the lowest and intermediate pretreatment doses of test compound were without appreciable effect, whereas the highest pretreatment dose of test compound, 32 mg/kg, produced an approximately 50% decrease in self-administration of the peak unit dose of i.v. cocaine. Reflecting averaged data, the lowest dose of test compound, 10 mg/kg, did not alter i.v. cocaine self-administration behavior in any of the four monkeys, and the intermediate pretreatment dose of test compound, 18 mg/kg, decreased self-administration of the peak unit dose of i.v. cocaine by approximately 50% in only one monkey, 89B013. The intermediate dose of test compound did not appreciably alter i.v. self-administration behavior in the remaining three subjects.

However, the highest pretreatment dose of test compound, 32 mg/kg, reduced self-administration of the peak unit dose of i.v. cocaine by 50% or more in each of the three monkeys in which it was studied.

Food-maintained behavior. Averaged for the group of monkeys, pretreatment doses of test compound had only inconsistent effects on food-maintained behavior during dose-ranging studies. The lowest dose of test compound, 10 mg/kg, decreased food-maintained responding only in the component following i.v. cocaine self-administration (Food 2) in two of four monkeys; 96D155 and 93N082 Food-maintained performance prior to or following i.v. cocaine self-administration (Food 1 and Food 2) was unchanged in the remaining two monkeys, 89B013 and RQ2215. The intermediate pretreatment dose of test compound, 18 mg/kg, also greatly decreased food-maintained behavior in the component following i.v. cocaine self-administration (Food 2) in two monkeys, 89B013 and 93N082 but did not change behavior in Food 2 in the remaining two subjects, 96D155 and RQ2215. Food-maintained behavior in the component prior to i.v. cocaine self-administration (Food 1) was not appreciably affected by 18 mg/kg of test compound in any monkey. Pretreatment with the highest dose of test compound (32 mg/kg) markedly decreased food-maintained performance prior to and following components of i.v. cocaine self-administration (Food 1 and Food 2) in one monkey, 93N082 but did not alter responding in either food component in the remaining two monkeys, 96D155 and RQ2215.

Effects of Test Compound (O-carbamoyl-(D)-phenylaminol) on Cocaine Self-Administration [Rapid Dose Effect Procedure]

Cocaine dose-effect data. Based on the above-described results of dose-ranging studies, test compound was studied further by evaluating how i-m. pretreatment with 32 mg/kg of test compound modified self-administration of a range of unit doses of i.v. cocaine. Monkey 898013 lost catheter patency prior to these experiments, and was replaced by monkey 97D105, The effects of test compound on self-administration of higher unit doses of cocaine (0.032-0.32 mg/kg/inj) differed qualitatively from its effects during the availability saline or the lower unit doses of cocaine (0.001-0.01 mg/kg/inj). Averaged for the group of monkeys, test compound increased responding during components of saline availability and during the availability of low unit doses of i.v. cocaine (0.001-0.01 mg/kg). On the other hand, test compound decreased self-administration behavior during availability of higher unit doses of i.v. cocaine (0.032-0.32 mg/kg).

The averaged data reflect effects of test compound that were consistent in three of four monkeys (96D155, 93N082, and 97D105). In these subjects, 32 mg/kg of test compound increased responding during components in which either saline or low unit doses of cocaine (0.001-0.01 mg/kg) were available for i.v. self-administration and reduced i.v. self-administration behavior during the availability of higher unit doses of cocaine on the descending segment of the inverted U-shaped dose-response curve. In the fourth monkey, RQ2215, the effects of pretreatment with 32 mg/kg of test compound were less prominent. Responding during the availability of saline or unit doses of i.v. cocaine ranging from 0.001-0.032 mg/kg/injection was inconsistently increased, whereas responding during the availability of the higher unit doses of 0.1 and 0.32 mg/kg cocaine was unchanged.

Food-maintained behavior. Averaged for the group of monkeys, 32 mg/kg of test compound produced marked (>50%) decreases in food-maintained responding during both Food 1 and Food 2 components of the session during rapid assessment of the dose-response curve for i.v. cocaine self-administration. The averaged results reflect decreases in food-maintained behavior in three of four subjects prior to or following i.v. cocaine self-administration (Food 1 and Food 2 components). Thus, responding was either moderately (40%) decreased or nearly eliminated for, respectively, monkey RQ22 15 or monkeys 93N082 and 97D 10 prior to i.v. cocaine self-administration (Food 1 component) and nearly eliminated for monkeys 96D155, 93N082, and 97D105 following i.v. cocaine self-administration (Food 2 component).

Results of dose-ranging studies with test compound indicate that i.m. pretreatment with 32 mg/kg of test compound markedly decreased self-administration behavior when the peak unit dose of i.v. cocaine was available throughout the session. Averaged across monkeys, this pretreatment dose of test compound did not consistently alter food-maintained behavior either prior to or following components in which i.v. cocaine was available for self-administration.

Subsequent studies confirmed these results and extended them by showing that, on average, test compound (32 mg/kg) increased responding during availability of saline or low to intermediate unit doses of i.v. cocaine and decreased self-administration of higher unit doses of i.v. cocaine. The combination of these effects resulted in a leftward and upward displacement of the descending portion of the cocaine dose-effect curve. The effects of test compound on cocaine self-administration were accompanied by disruptions in food-maintained performance that were more consistently observed across monkeys than during dose-ranging studies. These results indicate that i.m. pretreatment with test compound can decrease cocaine self-administration in a manner that is consistent with an agonist profile of action.

References Cited

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description. Such modifications and variations are intended to fall within the scope of the appended claims. The present invention is to be limited only by the terms of the appended claims, along with the full scope of equivalents to which such claims are entitled.

What is claimed is:

1. A method of treating drug addiction comprising the administration of a therapeutically effective amount of a compound having structural Formula (1) or a pharmaceutically acceptable salt or ester thereof, to a mammal in need of treatment:

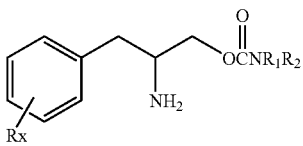

(I)

wherein,
R is hydrogen;
x is 1;
$R_1$ and $R_2$ are hydrogen; and
the compound having structural Formula (1) is an enantiomeric mixture wherein the (R) enantiomer of the compound having structural Formula (I) predominates.

2. The method of claim 1, wherein the enantiomer of (R)-(beta-amino-benzenepropyl) carbamate predominates to the extent of about 90% or greater.

3. The method of claim 2, wherein the enantiomer of (R)-(beta-amino-benzenepropyl) carbamate predominates to the extent of about 98% or greater.

4. The method of claim 1, wherein the addicted drug is at least one selected from the group consisting of nicotine, opioid, cocaine, amphetamine, methamphetamine, ethanol, heroin, morphine, phencyclidine (PCP), and methylene-dioxymethamphetamine (MDMA).

5. The method of claim 4, wherein the drug is cocaine.

6. The method of claim 4, wherein the therapeutically effective amount of the compound is from about 0.01 mg/kg/dose to about 300 mg/kg/dose.

7. A method of treating drug addiction comprising the administration of a therapeutically effective amount of a compound having structural Formula (I) or a pharmaceutically acceptable salt or ester thereof, to a mammal in need of treatment:

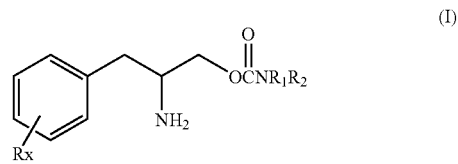

(I)

wherein,
R is hydrogen;
x is 1;
$R_1$ and $R_2$ are hydrogen; and
the compound having structural Formula (I) is an (R) enantiomer substantially free of other enantiomers.

8. The method of claim 7, wherein the addicted drug is at least one selected from the group consisting or nicotine, opioid, cocaine, amphetamine, methamphetamine, ethanol, heroin, morphine, phencyclidine (PCP), and methylene-dioxymethamphetamine (MDMA).

9. The method of claim 8, wherein the drug is cocaine.

10. The method of claim 8, wherein the therapeutically effective amount of the compound is from about 0.01 mg/kg/dose to about 300 mg/kg/dose.

* * * * *

UNITED STATES PATENT AND TRADEMARK OFFICE
CERTIFICATE OF CORRECTION

PATENT NO. : 8,232,315 B2
APPLICATION NO. : 12/492566
DATED : July 31, 2012
INVENTOR(S) : Sung James Lee and Susan Marie Melnick It is certified that error appears in the above-identified patent and that said Letters Patent is hereby corrected as shown below:

In the Specifications

Column 26, Line 29: Add the word --Time-- between the words "Total" and "Response"

In the Claims

Column 34, Claim 8, Line 46: Replace the word "or" with --of--

Signed and Sealed this
Thirteenth Day of August, 2013

Teresa Stanek Rea
*Acting Director of the United States Patent and Trademark Office*